(12) United States Patent
Ajima

(10) Patent No.: US 11,058,302 B2
(45) Date of Patent: Jul. 13, 2021

(54) ELECTRONIC DEVICE AND ESTIMATION SYSTEM

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 362 days.

(21) Appl. No.: 15/625,763

(22) Filed: Jun. 16, 2017

(65) Prior Publication Data

US 2018/0000356 A1 Jan. 4, 2018

(30) Foreign Application Priority Data

Jun. 30, 2016 (JP) .............................. JP2016-130531

(51) Int. Cl.

| *A61B 5/02* | (2006.01) |
|---|---|
| *A61B 5/00* | (2006.01) |
| *A61B 5/1495* | (2006.01) |
| *G16H 50/30* | (2018.01) |
| *A61B 5/021* | (2006.01) |
| *A61B 5/0537* | (2021.01) |
| *A61B 5/01* | (2006.01) |
| *A61B 5/145* | (2006.01) |

(52) U.S. Cl.
CPC ...... *A61B 5/02007* (2013.01); *A61B 5/02125* (2013.01); *A61B 5/1495* (2013.01); *A61B 5/6822* (2013.01); *A61B 5/7225* (2013.01); *A61B 5/7275* (2013.01); *G16H 50/30* (2018.01); *A61B 5/01* (2013.01); *A61B 5/0537* (2013.01); *A61B 5/14532* (2013.01); *A61B 5/681* (2013.01); *A61B 2560/0204* (2013.01); *A61B 2560/0431* (2013.01)

(58) Field of Classification Search
CPC ................ A61B 5/2007; A61B 5/7275; A61B 2560/0431; G16H 50/30
See application file for complete search history.

(56) References Cited

U.S. PATENT DOCUMENTS

| 2,555,422 | A | * | 6/1951 | Fernandez | ............. | A61B 5/164 |
| | | | | | | 600/502 |
| 3,154,066 | A | * | 10/1964 | Grindheim | ........... | A61B 5/0816 |
| | | | | | | 600/501 |
| 3,442,263 | A | * | 5/1969 | Pascaud | ............... | A61B 5/6831 |
| | | | | | | 600/503 |

(Continued)

FOREIGN PATENT DOCUMENTS

| JP | H0542111 A | 2/1993 |
| JP | 2001161650 A | 6/2001 |

(Continued)

OTHER PUBLICATIONS

J. Hernandez, Y. Li, J. M. Rehg and R. W. Picard, Cardiac and Respiratory Parameter Estimation Using Head-mounted Motion-sensitive Sensors, May 18, 2015, EAI Endorsed Transactions on Pervasive Health and Technology, vol. 01, Issue 1 (Year: 2015).*

*Primary Examiner* — Sean P Dougherty
*Assistant Examiner* — Connor William Blake
(74) *Attorney, Agent, or Firm* — Studebaker & Brackett PC

(57) ABSTRACT

An electronic device includes a sensor unit configured to acquire a pulse wave of a subject's carotid artery and a controller configured to estimate a condition of the subject's carotid artery based on the pulse wave acquired by the sensor unit.

5 Claims, 10 Drawing Sheets

(56) References Cited

U.S. PATENT DOCUMENTS

| | | | | |
|---|---|---|---|---|
| 3,641,528 | A * | 2/1972 | Dirks | G11B 17/038 360/75 |
| 4,129,124 | A * | 12/1978 | Thalmann | A61B 5/02416 600/479 |
| 4,409,983 | A * | 10/1983 | Albert | A61B 5/02438 600/502 |
| 4,971,062 | A * | 11/1990 | Hasebe | A61B 5/02427 600/473 |
| 5,293,874 | A | 3/1994 | Takahashi et al. | |
| 6,491,647 | B1 * | 12/2002 | Bridger | A61B 5/021 128/900 |
| 6,592,528 | B2 | 7/2003 | Amano | |
| 8,346,328 | B2 * | 1/2013 | Mannheimer | A61B 5/02416 600/310 |
| 8,352,004 | B2 * | 1/2013 | Mannheimer | A61B 5/6843 600/310 |
| 2002/0072860 | A1 * | 6/2002 | Amano | A61B 5/021 702/19 |
| 2003/0167014 | A1 * | 9/2003 | Ogura | A61B 5/021 600/513 |
| 2003/0199776 | A1 * | 10/2003 | Narimatsu | A61B 5/022 600/494 |
| 2006/0258945 | A1 * | 11/2006 | Nishii | A61B 5/02438 600/500 |
| 2007/0032749 | A1 * | 2/2007 | Overall | A61B 5/02444 600/595 |
| 2016/0058385 | A1 * | 3/2016 | Ajima | A61B 5/02007 600/485 |
| 2017/0007184 | A1 * | 1/2017 | Kang | A61B 5/7435 |
| 2017/0277858 | A1 * | 9/2017 | Okubo | G16H 50/20 |
| 2018/0146869 | A1 * | 5/2018 | Zhang | A61B 5/02007 |
| 2020/0129123 | A1 * | 4/2020 | Ajima | A41D 13/00 |
| 2020/0155076 | A1 * | 5/2020 | Konishi | A61B 5/1102 |
| 2020/0345244 | A1 * | 11/2020 | Ajima | A61B 5/02108 |

FOREIGN PATENT DOCUMENTS

| | | | |
|---|---|---|---|
| JP | 2005-000390 A | 1/2005 | |
| JP | 2016-087209 A | 5/2016 | |
| WO | 0170106 A1 | 9/2001 | |
| WO | WO-2014171465 A1 * | 10/2014 | ........... A61B 5/6898 |

* cited by examiner

ELECTRONIC DEVICE AND ESTIMATION SYSTEM

TECHNICAL FIELD

The present disclosure relates to an electronic device and an estimation system that estimate health conditions of a subject from measured biological information.

BACKGROUND

Devices that diagnose diseases such as arteriosclerosis of a subject have been known.

SUMMARY

An electronic device according to one embodiment comprises a sensor unit configured to acquire a pulse wave of a subject's carotid artery and a controller configured to estimate a condition of the subject's carotid artery based on the pulse wave acquired by the sensor unit.

An estimation system according to one embodiment comprises an electronic device that includes a sensor unit configured to acquire a pulse wave in a subject's carotid artery and an estimation device that includes a controller configured to estimate a condition of the subject's carotid artery based on the pulse wave acquired by the sensor unit.

DETAILED DESCRIPTION

Ultrasonic diagnostic equipment known in the art diagnoses diseases such as arteriosclerosis based on ultrasonic images acquired through irradiation of a predetermined position of a subject's neck with ultrasonic waves. Unfortunately, in the ultrasonic diagnostic equipment known in the art, unclear ultrasonic images make it difficult to acquire correct diagnosis results. The electronic device and the estimation system according to the present disclosure allows for a stable and easy estimation of the carotid artery condition.

Some embodiments will be described below with reference to the accompanying drawings.

Figure 1:
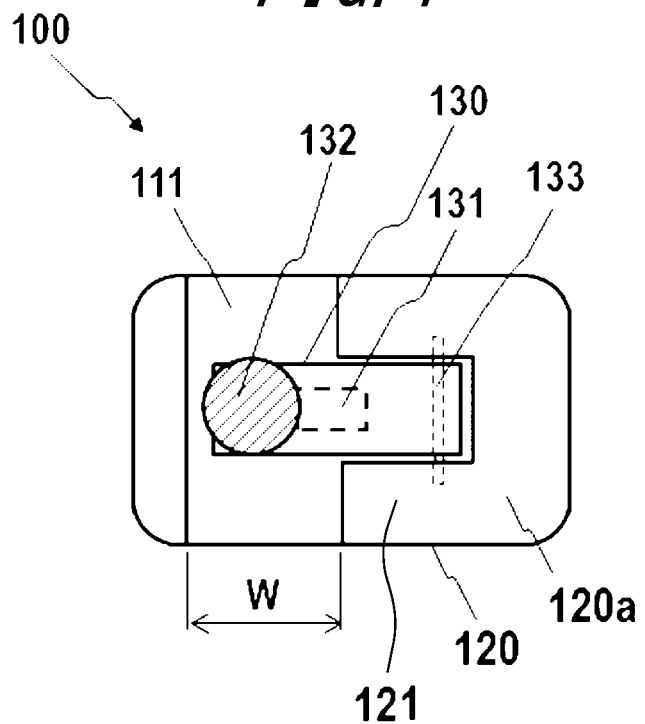
FIG. 1 is a schematic diagram illustrating a schematic configuration of an electronic device according to one embodiment.
Figure 2:
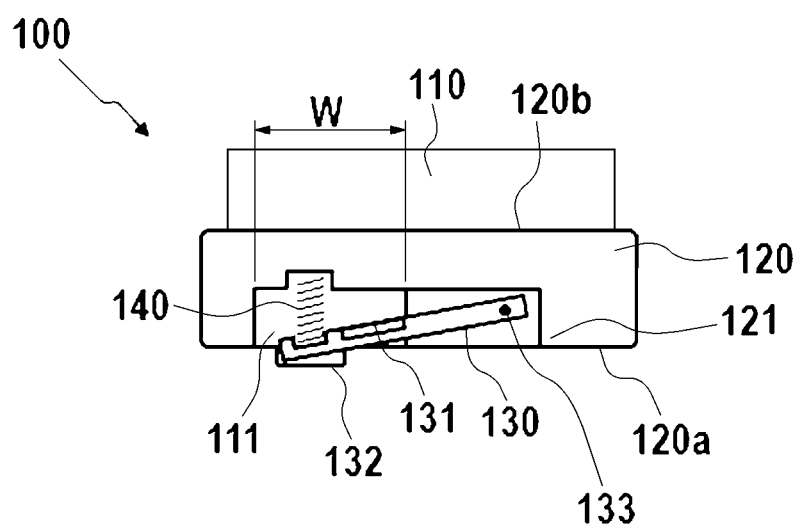
FIG. 2 is a cross-sectional diagram illustrating a schematic configuration of the electronic device of FIG. 1.

FIG. 1 is a schematic diagram illustrating a schematic configuration of an electronic device according to one embodiment. FIG. 2 is a cross-sectional diagram illustrating a schematic configuration of the electronic device of FIG. 1. An electronic device 100 includes a gripper 110 and a measurement unit 120. FIG. 1 is a diagram of the electronic device 100 viewed from the back side 120a that is put to a measured part.

The subject measures his or her biological information while grasping the electronic device 100 and putting the measurement unit 120 to the measured part. The biological information to be measured with the electronic device 100 is a pulse wave of the subject that can be measured with the measurement unit 120. In one embodiment, to acquire a pulse wave, the subject grasps the electronic device 100 so that the measurement unit 120 will come in contact with a position of the subject's carotid artery where a pulse wave can be acquired.

In one embodiment, the subject puts the electronic device 100 to his or her neck so that the back side 120a of the measurement unit 120 will come in contact with the measured part, and measures a pulse wave. The electronic device 100 measures a pulse wave of the blood flowing through the carotid artery at the subject's neck.

The measurement unit 120 has the back side 120a that comes in contact with the subject's neck during measurement of a pulse wave and a front side 120b on the side opposite to the back side 120a. The measurement unit 120 has an opening 111 on the back side 120a. A sensor unit 130 has a first end that comes in contact with the subject's neck and a second end that comes in contact with the measurement unit 120. The first end of the sensor unit 130 projects from the opening 111 to the back side 120a with no pressure applied on an elastic member 140. The first end of the sensor unit 130 has a pulse contact unit 132. The first end of the sensor unit 130 is displaceable in the direction substantially vertical to the plane of the back side 120a. The second end of the sensor unit 130 is in contact with the measurement unit 120 via a shaft 133. The measurement unit 120 includes a sensor support 121 that the back side 120a comes in contact with the neck during measurement of a pulse wave to stabilize the contact condition of the electronic device 100 with the neck.

The first end of the sensor unit 130 is in contact with the measurement unit 120 via the elastic member 140. The first end of the sensor unit 130 is displaceable relative to the measurement unit 120. The elastic member 140 includes a spring, for example. The elastic member 140 is not limited to a spring, and may be other elastic members, such as resin and sponge.

A controller, a memory, a communication interface, a power supply, a notification interface, a circuit for operating these units and a cable for connecting these units or the like may be disposed in the measurement unit 120.

The sensor unit 130 includes an angular velocity sensor 131 configured to detect a displacement of the sensor unit 130. The angular velocity sensor 131 needs only to detect an angular displacement of the sensor unit 130. Besides one or more angular velocity sensors 131, the sensor unit 130 may include one or more other sensors, such as acceleration sensors, angular sensors and other motion sensors.

Figure 3:
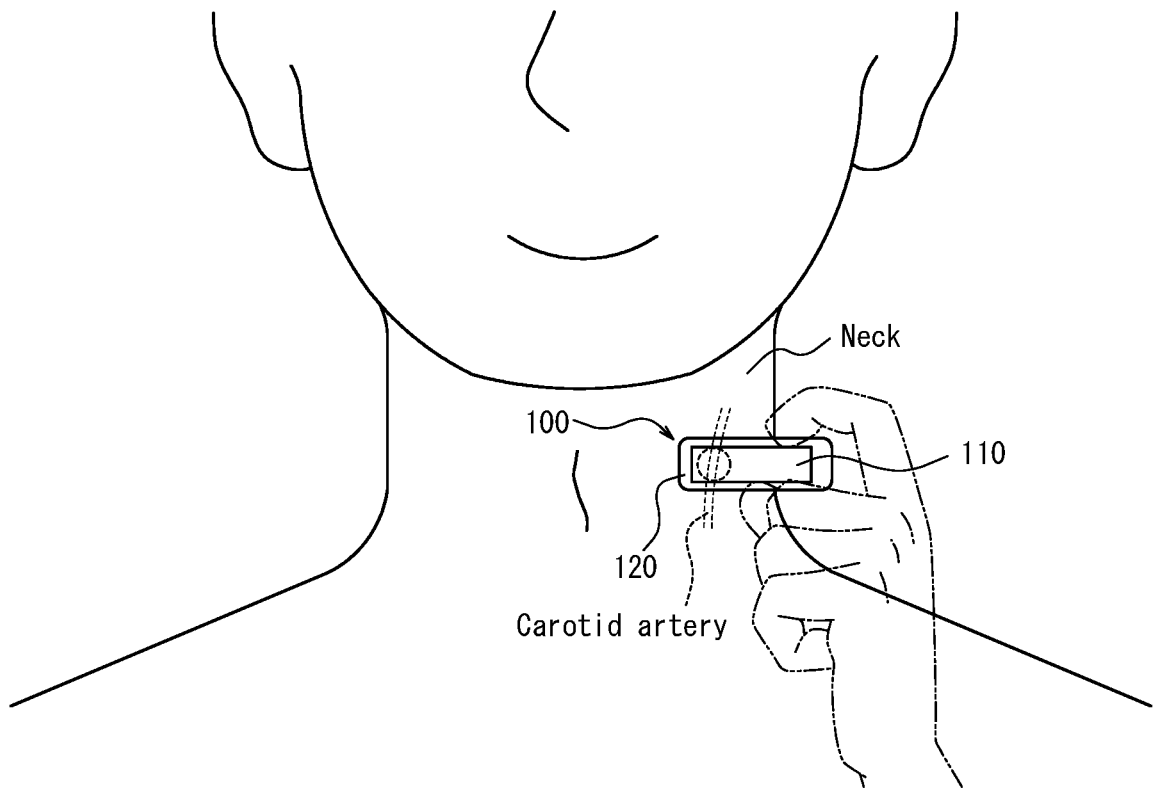
FIG. 3 is a diagram illustrating an example of the electronic device of FIG. 1 in use.

FIG. 3 illustrates an example of the electronic device 100 in use by the subject. In FIG. 3, the position of the carotid artery is schematically illustrated for explanation. The subject grasps the gripper 110 of the electronic device 100 with his or her fingers so that the measurement unit 120 will come in contact with the measured part. In one embodiment, in particular, the subject grasps the electronic device 100 so that the pulse contact unit 132 will come in contact with his or her skin over the carotid artery. When the subject grasps the electronic device 100 so that the sensor support 121 will come in contact with his or her sternocleidomastoid muscle, the pulse contact unit 132 can easily come in contact with the position under which the carotid artery is located in a stable manner.

With the electronic device 100 being in contact with the subject's neck, the first end of the sensor unit 130 is in contact with the subject's neck so that the skin over the subject's carotid artery will be pressed by an appropriate pressure caused by an elastic force of the elastic member 140 disposed between the measurement unit 120 and the sensor unit 130. The sensor unit 130 is displaced in response to the movement of the subject's carotid artery, that is, a pulsation. The angular velocity sensor 131 detects a displacement of the sensor unit 130, and thus acquires a pulse wave of the carotid artery. A pulse wave is a change in the volume of the vessel over time caused by the blood flowing into the vessel, which is captured from a body surface as a waveform.

Referring to FIG. 2 again, the first end of the sensor unit 130 projects from the opening 111 with no pressure applied on the elastic member 140. When the subject puts the electronic device 100 to his or her neck, the first end of the sensor unit 130 comes in contact with the skin of the subject's neck, and the elastic member 140 expands and contracts in response to pulsation, thus the first end of the sensor unit 130 is displaced. The elastic member 140 with an appropriate elastic modulus is used so that pulsation will not be disturbed and expansion and contraction in response to pulsation will be achieved. The opening width W of the opening 111 may be larger enough than the blood vessel diameter, or according to one embodiment, larger enough than the carotid artery diameter. So the opening portion 111 is provided in the measuring portion 120, the back side 120a of the measurement unit 120 does not press the carotid artery with the electronic device 100 being in contact with the neck. Thus the electronic device 100 can acquire a pulse wave with less noise, and the measuring accuracy of pulse wave is improved.

Although FIG. 3 illustrates an example in which the subject puts the electronic device 100 to his or her neck to acquire a pulse wave of his or her carotid artery, the subject may put the electronic device 100 to his or her wrist to acquire a pulse wave of the blood flowing into his or her radial artery or ulnar artery. Specifically, the subject may softly press the position of the radial artery or the ulnar artery with the pulse contact unit 132 to measure a pulse wave.

Figure 4:
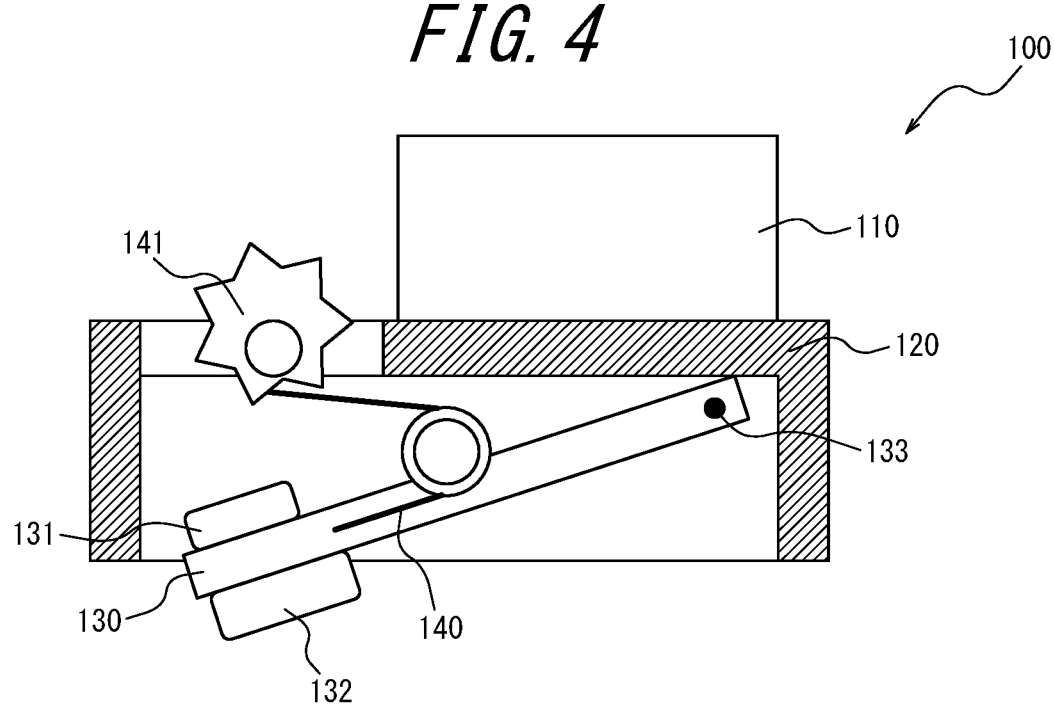
FIG. 4 is a cross-sectional diagram illustrating a schematic configuration of another example of the electronic device.

The configuration of the electronic device 100 is not limited to that illustrated in FIG. 2. FIG. 4 is a cross-sectional diagram illustrating a schematic configuration of another example of the electronic device 100. The electronic device 100 illustrated in FIG. 4 includes a torsion coil spring as the elastic member 140. The torsion coil spring has two arms. The first arm is connected to the sensor unit 130 and the second arm is connected to the pressure adjustment unit 141. The pressure adjustment unit 141 has a mechanism that can adjust a pressure applied from the sensor unit 130 to the measured part via the elastic member 140. The pressure adjustment unit 141 includes a rotation mechanism that has an eccentric shaft, for example, and a pressure applied by the elastic member 140 can be adjusted by rotation of the rotation mechanism. When the electronic device 100 has the pressure adjustment unit 141, a pressure applied from the sensor unit 130 to the measured part can be adjusted depending on the subject, and thus a pulse wave can be measured with a higher accuracy depending on each subject.

Figure 5:
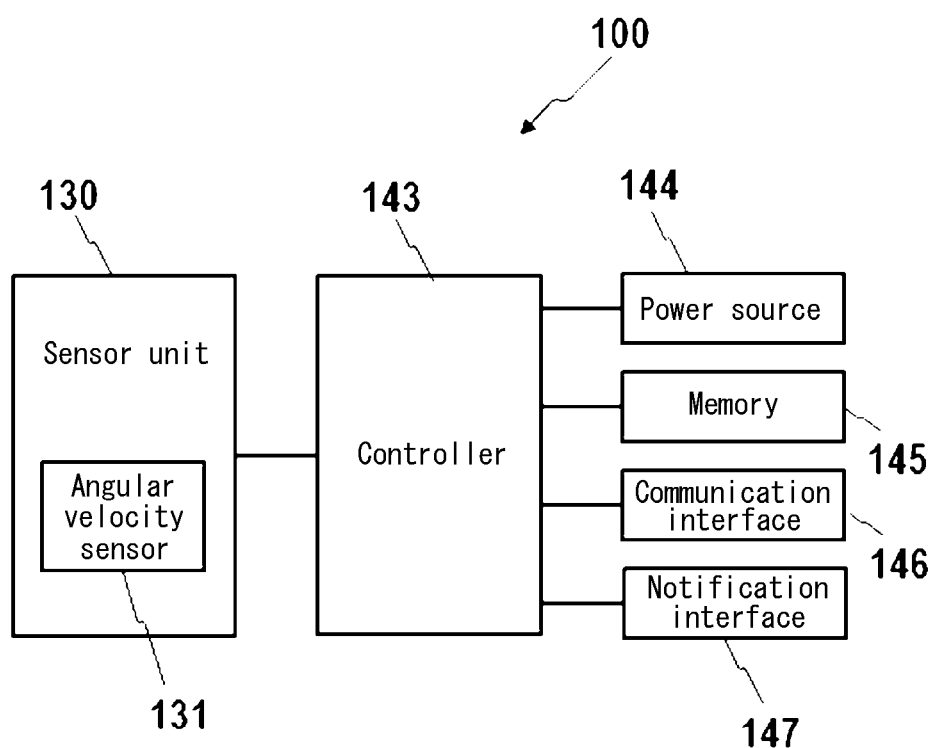
FIG. 5 is a functional block diagram illustrating a schematic configuration of the electronic device of FIG. 1.

FIG. 5 is a functional block diagram of the electronic device 100. The electronic device 100 includes the sensor unit 130, a controller 143, a power supply 144, a memory 145, a communication interface 146 and a notification interface 147. In one embodiment, the controller 143, the power supply 144, the memory 145, the communication interface 146 and the notification interface 147 may be included in the measurement unit 120 or the gripper 110.

The sensor unit 130 includes the angular velocity sensor 131 and detects a pulsation from the measured part to acquire a pulse wave.

The controller 143 is a processor that controls and manages the entire electronic device 100 in addition to each functional block of the electronic device 100. The controller 143 is a processor that estimates the condition of the subject's carotid artery based on the acquired pulse wave. The controller 143 comprises a processor such as a central processing unit (CPU) that implements a program for defining control procedures and a program for estimating the condition of the carotid artery. These programs are stored in a storage medium, such as the memory 145. The controller 143 may notify data to the notification interface 147.

The power supply 144 includes a lithium-ion battery and a control circuit for charging and discharging the battery and supplies power to the entire electronic device 100. The power supply 144 is not limited to a secondary battery, such as a lithium-ion battery, and may be a primary battery, such as a button battery.

The memory 145 stores programs and data. The memory 145 may include a non-transitory medium, such as a semiconductor storage medium and a magnetic storage medium. The memory 145 may include several types of storage media. The memory 145 may include a combination of a portable storage medium, such as a memory card, an optical disc or a magnetic optical disc, and a reading device for a storage medium. The memory 145 may include a storage device, such as a random access memory (RAM) that can be used as a temporary storage area. The memory 145 stores various kinds of information or programs for operating the electronic device 100 and serves as a work memory. The memory 145 may store the measurement results of pulse wave acquired by the sensor unit 130, for example.

The communication interface 146 transmits and receives various data through wired or wireless communication with an external device. The communication interface 146 communicates with an external device that stores the biological information of the subject to manage his or her health condition, for example. The communication interface 146 transmits the measurement results of pulse wave measured by the electronic device 100 or the health condition estimated by the electronic device 100 to the external device.

The notification interface 147 notifies the information with sound, vibration, image or the like. The notification interface 147 may include a speaker, an oscillator and a display device. The display device may be a liquid crystal display (LCD), an organic electro-luminescence display (OELD) or an inorganic electro-luminescence display (IELD). In one embodiment, the notification interface 147 notifies the condition of the subject's carotid artery, for example.

Figure 6:
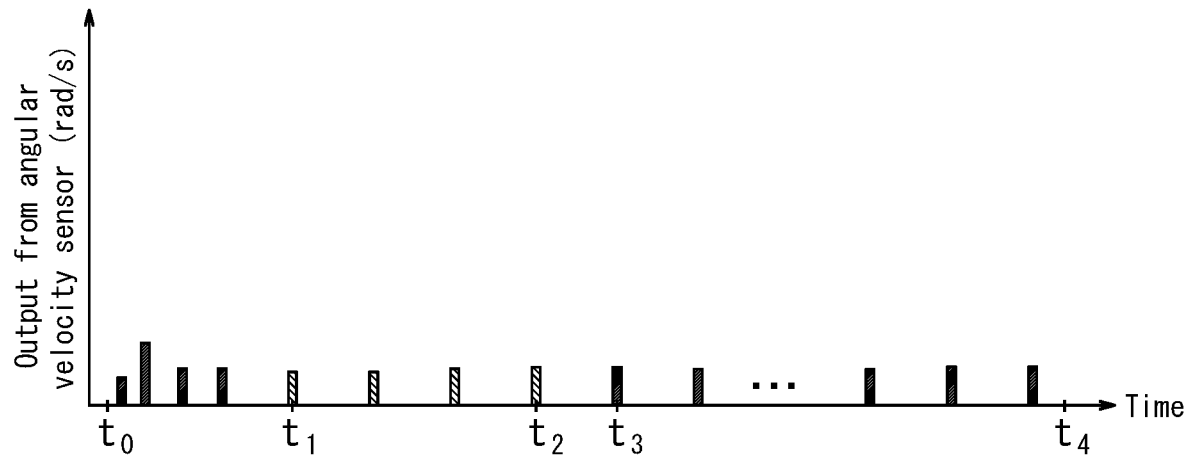
FIG. 6 is a schematic diagram illustrating pulse wave measurement processing with the electronic device of FIG. 1.
Figure 7:
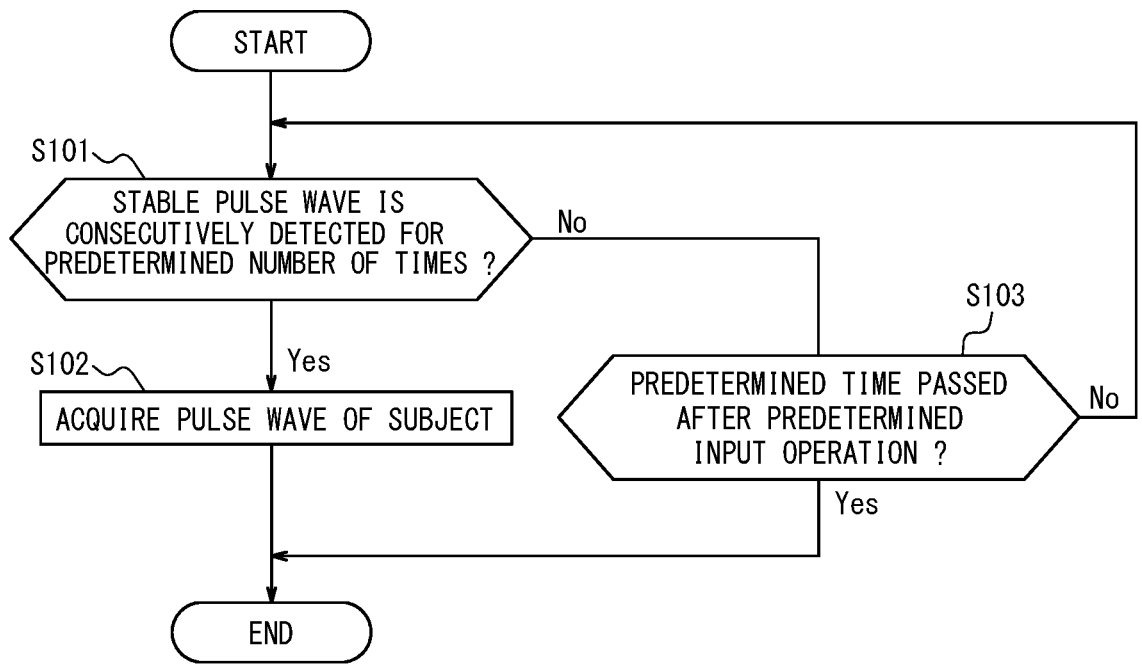
FIG. 7 is a flow chart illustrating a procedure of the pulse wave measurement processing with the electronic device of FIG. 1.

Next, the measurement processing of pulse wave with the electronic device 100 will be described in detail. FIG. 6 is a schematic diagram illustrating the measurement processing of pulse wave with the electronic device 100. FIG. 7 is a flow chart illustrating the measurement processing procedures of pulse wave with the electronic device 100. In FIG. 6, the horizontal axis represents time and the vertical axis schematically represents output (rad/sec) of the angular velocity sensor 131 based on pulse wave. In FIG. 6, the output of the angular velocity sensor 131 represents only peaks of each pulse wave.

The subject performs a predetermined input operation to the electronic device 100 at the time $t_0$ to start the pulse wave measurement processing. That is, the electronic device 100 starts measuring pulse wave at the time $t_0$. After performing the predetermined input operation to start the measurement processing of pulse wave, the subject grasps the gripper 110 and puts the measurement unit 120 to his or her neck. When the subject performs a predetermined input operation to start the measurement processing of pulse wave, the electronic device 100 starts the flow illustrated in FIG. 7.

In the electronic device 100, when the measurement processing of pulse wave is started, the controller 143 detects outputs of the angular velocity sensor 131 in response to pulsation of the carotid artery. During a predetermined period of time (from $t_0$ to $t_1$ of FIG. 6) immediately after the measurement is started, the subject adjusts the contact position on his or her neck with the electronic device 100, and thus outputs of the angular velocity sensor 131 are unstable. Pulse waves cannot be accurately acquired during this period of time. Thus, the electronic device 100 may not use pulse waves measured during this period of time for estimation of the condition of the carotid artery. For example, the electronic device 100 may not store pulse waves measured during this period of time in the memory 145.

The controller 143 determines whether stable pulse waves have been detected for a predetermined number of times in succession after the start of the pulse wave measurement processing (step S101 of FIG. 7). The predetermined number of times is not limited to four as illustrated in FIG. 6. For example, a stable pulse wave refers to a pulse wave having variations in peak outputs of each pulse wave and/or variations in intervals between each pulse wave within a predetermined error range. The predetermined error range between peaks includes ±150 msec., but not limited thereto. FIG. 6 illustrates an example where the controller 143 detects pulse waves that variations of the interval between each peaks of the pulse waves is within ±150 msec in four consecutive during the period from the time t1 to the time t2.

The controller 143 starts acquiring pulse waves (step S102) when it determines that stable pulse waves have been consecutively detected for a predetermined number of times after the start of the pulse wave measurement processing (Yes in step S101 of FIG. 7). That is, the controller 143 acquires pulse waves to be used to estimate the carotid artery condition. The time of start acquiring pulse waves is the time $t_3$ of FIG. 6, for example. The controller 143 may store pulse waves acquired in the above described manner in the memory 145. The electronic device 100 starts acquiring pulse waves when determining that it has consecutively detected stable pulse waves for a predetermined number of times, and thus a false detection that may occur when the subject does not actually put the electronic device 100 to him or her skin can be prevented easily.

When the termination conditions for acquiring pulse waves are satisfied after the start of acquiring pulse waves, the controller 143 terminates acquisition of pulse waves. The termination conditions may include an elapse of a predetermined period of time after the start of acquiring pulse waves and when pulse waves are acquired for a predetermined number of pulses, for example. The termination conditions are not limited to these examples and other conditions may be appropriately set. In the example illustrated in FIG. 6, the controller 143 terminates acquisition of pulse waves at the time $t_4$ after a predetermined time (e.g. 8 or 15 seconds) from the time $t_3$. Thus the flow illustrated in FIG. 7 ends.

When the controller 143 determines that stable pulse waves have not been consecutively detected after the start of the pulse wave measurement processing (No in step S101 of FIG. 7), it determines whether a predetermined period of time has elapsed after the predetermined input operation for starting the pulse wave measurement processing (step S103).

When the controller 143 determines that the predetermined period of time (e.g. 30 seconds) has not been elapsed after the predetermined input operation for starting the pulse wave measurement processing (No in step S103), the flow of FIG. 7 proceeds to step S101.

Meanwhile, when the controller 143 cannot detect stable pulse waves after the predetermined period of time has elapsed from the predetermined input operation for starting the pulse wave measurement processing (Yes in step S103), it automatically terminates the measurement processing (time out) and the flow of FIG. 7 ends.

Figure 8:
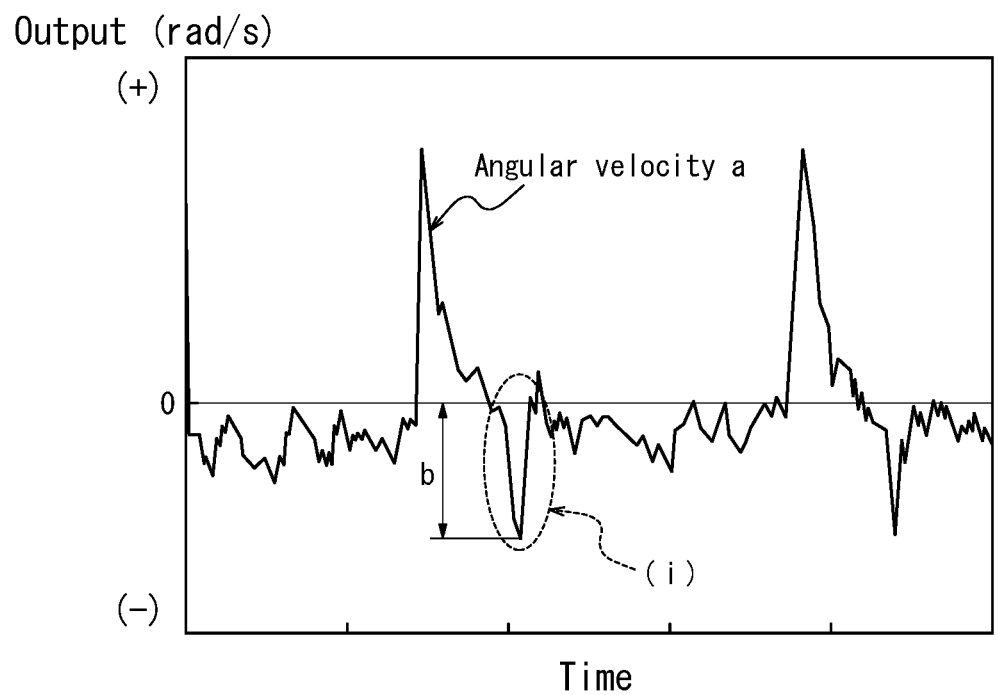
FIG. 8 is a diagram illustrating an example of pulse wave acquired with the electronic device of FIG. 1.

FIG. 8 is a diagram illustrating an example of pulse wave acquired by the electronic device 100 in accordance with the flow of FIG. 7. The electronic device 100 detects a displacement of the sensor unit 130 caused by pulsation from outputs of the angular velocity sensor 131. FIG. 8 represents the pulse wave acquired with the electronic device 100 by using outputs of the angular velocity sensor 131 over time. In FIG. 8, the reference position of the outputs of the angular velocity sensor 131 is a position where the surface of the pulse contact unit 132 that comes in contact with the subject is flush with the surface of the sensor support 121 that comes in contact with the subject (i.e. the back side 120*a* of the measurement unit 120). In FIG. 8, the side of the pulse contact unit 132 receding from the back side 120*a* is indicated as a positive direction (+) and the side projecting from the back side 120*a* is indicated as a negative direction (−).

The inventor has found that the waveform acquired with the electronic device 100 and illustrated as an example in FIG. 8 is similar to the signal (laser doppler signal) acquired with a diagnosis device that uses ultrasonic waves. The inventor has arrived at the possibility of estimating the condition of the subject's carotid artery by using waveforms acquired with the electronic device 100 instead of using laser doppler signals.

Now the processing for estimating the condition of the subject's carotid artery with the electronic device 100 will be described in detail. The electronic device 100 calculates the dicrotic notch (DN) to estimate the carotid artery condition. DN is referred to also as duplicated incisure. DN is represented by the decline of the pulse contact unit 132 in the negative direction as illustrated by (i) in the waveform of FIG. 8. The controller 143 of the electronic device 100 may calculate the DN of the declined portion indicated by (i) by using the decline amount b.

As the condition of the carotid artery, the electronic device 100 estimates the degree of arteriosclerosis in the carotid artery, for example, based on the calculated DN. A large dependence of the degree of arteriosclerosis on the condition of a plaque formed by a hypertrophied inner lining of blood vessel has been known. The electronic device 100 can estimate the degree of arteriosclerosis based on an estimation of the plaque condition.

The pulse wave acquired with the electronic device 100 changes depending on the condition of plaque in the carotid artery, such as the number of plaques and the degree of thickened plaque. Thus, DN changes depending on the plaque condition in the carotid artery. Since DN shows the effects of carotid artery, the electronic device 100 can estimate the plaque condition based on the calculated DN.

Specifically, the electronic device 100 estimates a plaque score as the plaque condition based on a relationship between DNs previously stored in the memory 145 and the plaque score, for example. The plaque score is an index of the height of plaque present in the carotid artery. The plaque score may be the sum of intima-media thicknesses (IMTs) of 1.1 mm or more present in the range of 1.5 cm on the periphery (head) side and 4.5 cm on the nerve (trunk) side along the carotid artery from a base point, which is a branch of each of the right and the left carotid arteries, for example.

Figure 9:
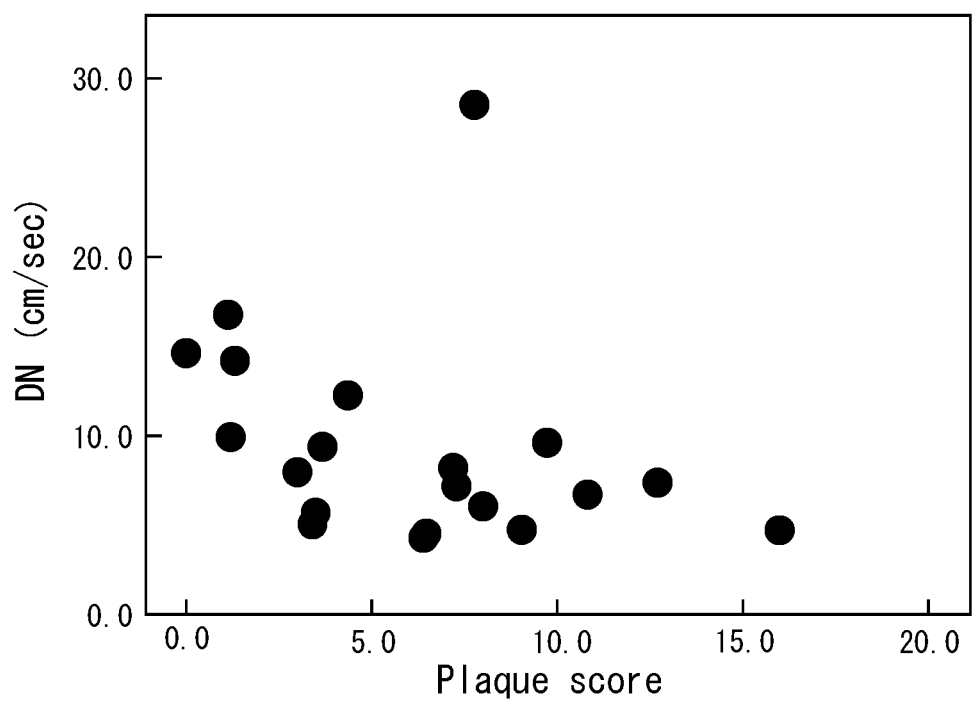
FIG. 9 is a diagram illustrating a relationship between dicrotic notch and plaque score.

FIG. 9 is a diagram illustrating a relationship between the DN and the plaque score. As illustrated in FIG. 9, the DN is negatively correlated with the plaque score. The electronic device 100 uses the calculated DN and calculates the plaque score of the subject based on the relationship between the DN and the plaque score illustrated in FIG. 9, for example. Thus, the electronic device 100 can estimate the plaque score as the condition of carotid artery. The electronic device 100 estimates the degree of arteriosclerosis based on the plaque score that indicates the plaque condition.

The electronic device 100 may notify the information on the estimated degree of arteriosclerosis from the notification interface 147. The electronic device 100 may associate the information on the degree of estimated arteriosclerosis with the information on the plaque condition, such as a plaque score, and notify it.

Thus, the electronic device 100 according to one embodiment can estimate the condition of the subject's carotid artery based on the pulse wave of carotid artery acquired by displacement of the angular velocity sensor 131. When the condition of carotid artery is estimated with a diagnosis device that uses ultrasonic waves, for example, the location of the carotid artery to be examined changes depending on how a probe is applied to the measured part, which causes changes or unclear images on acquired ultrasonic images. Thus, the diagnosis device using ultrasonic waves may have difficulties in acquiring correct diagnosis results. Whereas, the electronic device 100 according to the present embodiment estimates the condition of carotid artery based on the pulsation of carotid artery, and thus it can estimate the condition of carotid artery in more stable manner compared to the diagnosis device that uses ultrasonic waves.

The subject may acquire pulse waves of carotid artery under predetermined conditions that allow the subject to acquire favorable DNs easily. For example, after the meal, pulse waves are affected by reflected waves that are reflected by a vessel, and thus favorable DNs are difficult to be acquired. Thus the subject may acquire pulse waves of carotid artery before the meal.

The subject can estimate the blood fluidity and the condition of the carbohydrate metabolism or the lipid metabolism with the electronic device 100. For example, the subject puts the electronic device 100 to his or her neck, which is a measured part. The electronic device 100 detects a displacement of the sensor unit 130 acquired with the angular velocity sensor 131 based on a displacement of the pulse contact unit 132 put to the position under which the subject's carotid artery is present, and acquires pulse waves. The controller 143 calculates the index based on the propagating phenomenon of the pulse wave and estimates the subject's blood fluidity and the condition of the carbohydrate metabolism or the lipid metabolism.

Figure 10:
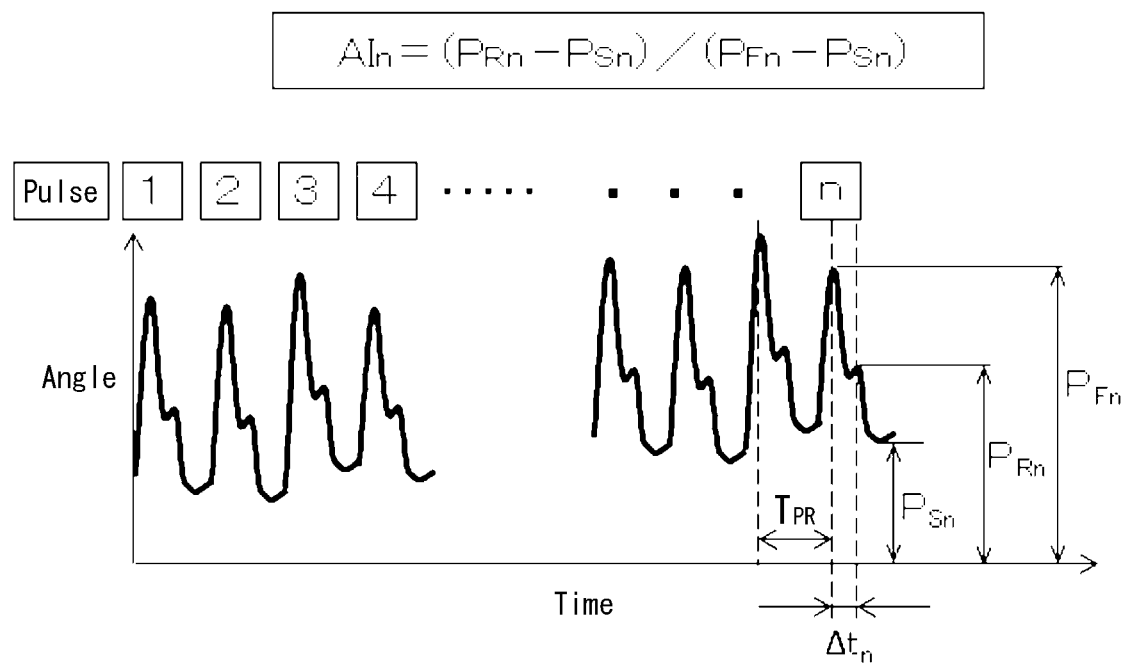
FIG. 10 is a diagram illustrating an example of pulse wave acquired by a sensor unit.

FIG. 10 is a diagram illustrating an example of pulse wave acquired with the electronic device 100 at the neck. FIG. 10 illustrates a case where the angular velocity sensor 131 is used as a detection means of pulsation. In FIG. 10, the angular velocities acquired by the angular velocity sensor 131 are integrated. The horizontal axis represents time and the vertical axis represents angle. The acquired pulse waves may include noise caused by the body motion of the subject, for example. Thus a filter for removing direct current (DC) components may be used for correction and only pulsation components may be extracted.

A method of calculating the index based on the pulse wave from the acquired pulse wave will be described by using FIG. 10. The pulse wave propagation is a phenomenon in which pulsations caused by the blood pumped out of the heart pass along the artery wall or through the blood. The pulsations caused by the blood pumped out of the heart reach the periphery of limbs as forward waves, and a part thereof are reflected by some portions of blood vessel, such as vessel bifurcations and portions where vessel diameter changes, and return as reflected waves. The index based on pulse wave includes a pulse wave velocity (PWV) of forward wave, a height of reflected wave of the pulse wave $P_R$, a time difference $\Delta t$ between the forward wave and the reflected wave of pulse wave and an augmentation index (AI) represented by the ratio between the height of forward wave and the height of reflected wave of pulse wave.

The pulse wave illustrated in FIG. 10 is the pulse of the user for n times, and n is an integer greater than or equal to 1. The pulse wave is a composite wave composed of a forward wave caused by pumping out of blood from the heart and a reflected wave generated from the vessel bifurcation and the portion where the vessel diameter changes overlapped with each other. In FIG. 10, $P_{Fn}$ represents the height of peak of the pulse wave by the forward wave for each pulse, $P_{Rn}$ represents the height of pulse wave by the reflected wave for each pulse, and $P_{Sn}$ represents the minimum pulse wave value for each pulse. In FIG. 10, $T_{PR}$ represents the interval between pulse peaks.

The index based on pulse wave is calculated by quantifying the information acquired from the pulse wave. For example, PWV, which is one of indices based on pulse wave, is calculated based on the difference in propagation time between pulse waves measured at two regions to be examined, such as a neck and a wrist, and the distance between two points. Specifically, PWV is acquired by synchronizing the pulse waves at two points (e.g. a neck and a wrist) of the artery and is calculated by dividing the difference in distance (L) between two points by the difference in time (PTT) between pulse waves at two points. For example, the height of reflected wave $P_R$, which is one of indices based on pulse wave, may be found by calculating the height of peak $P_{Rn}$ of the pulse wave by the reflected wave or by calculating $P_{Rave}$, which is the average for n times. For example, the time difference Δt between the forward wave and the reflected wave of the pulse wave, which is one of indices based on pulse wave, may be found by calculating the time difference $Δt_n$ of a predetermined pulse, or by calculating $Δt_{ave}$, which is the average of time differences for n times. For example, AI, which is one of indices based on pulse wave, is calculated by dividing the height of reflected wave by the height of forward wave, and is represented by $AI_n=(P_{Rn}-P_{Sn})/(P_{Fn}-P_{Sn})$. $AI_n$ represents the AI for each pulse. AI may be an index based on pulse wave, and found by measuring the pulse wave for a few seconds and calculating the average $AI_{ave}$ of $AI_n$ (n is an integer ranging from 1 to n) for each pulse.

The pulse wave propagation velocity PWV, the height of reflected wave $P_R$, the time difference between the forward wave and the reflected wave Δt and AI change depending on the hardness of the blood vessel wall, and thus can be used for estimating the arteriosclerosis condition. For example, when the blood vessel wall is hard, the pulse wave propagation velocity PWV increases. For example, when the blood vessel wall is hard, the height of reflected wave $P_R$ increases. For example, when the blood vessel wall is hard, the time difference Δt between the forward wave and the reflected wave decreases. For example, when the blood vessel wall is hard, AI increases. The electronic device 100 can estimate the blood fluidity (viscosity) as well as the arteriosclerosis condition by using these indices based on pulse wave. For example, the electronic device 100 can estimate the change in blood fluidity based on the change in the index based on pulse wave acquired from the same measured part of the same subject and acquired in the period of time during which the arteriosclerosis condition remains almost unchanged (e.g. within a few days). The blood fluidity indicates the degree of ease of blood's flow. For example, when the blood fluidity is low, the pulse wave propagation velocity PWV decreases, and when the blood fluidity is low, the height of the reflected wave $P_R$ decreases. Further, when the blood fluidity is low, the time difference Δt between the forward wave and the reflected wave increases and AI decreases.

In one embodiment, as an example of an index based on pulse wave, the electronic device 100 calculates the pulse wave propagation velocity PWV, the height of reflected wave $P_R$, the time difference Δt between the forward wave and the reflected wave and AI. However, an index based on the pulse wave is not limited thereto. For example, the electronic device 100 may use a second peak of systolic blood pressure as an index based on pulse wave.

Figure 11:
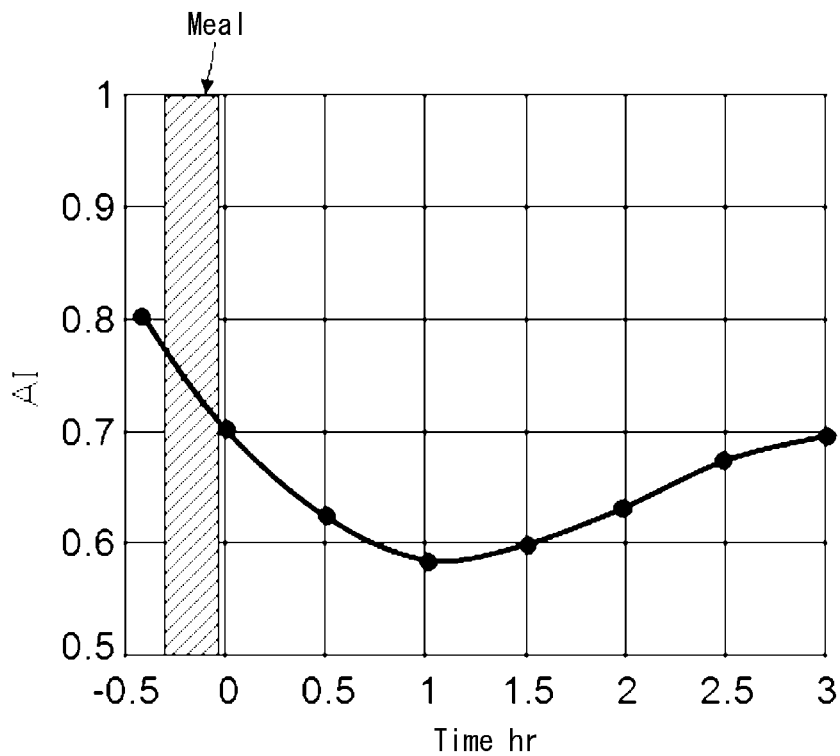
FIG. 11 is a diagram illustrating a change in calculated AIs over time.

FIG. 11 is a diagram illustrating a change in the calculated AI over time. In one embodiment, the pulse wave was acquired for 5 seconds with the electronic device 100 that includes the angular velocity sensor 131. The controller 143 calculated the AI for each pulse from the acquired pulse wave and their average value, $AI_{ave}$, as well. In one embodiment, the electronic device 100 acquired pulse waves at multiple timings including before and after the meal, and as an example of an index based on pulse wave, calculated the average of AIs (hereinafter referred to as AI). In FIG. 11, the horizontal axis represents a lapse of time with the first measurement time after the meal defined as 0, and the vertical axis represents AI calculated based on pulse wave acquired at the first measurement time.

The electronic device 100 acquired pulse waves before the meal, immediately after the meal and every half hour after the meal and calculated multiple AIs based on each pulse wave. The AI calculated based on pulse wave acquired before the meal was about 0.8. Compared to this, the AI acquired after the meal was small, and the AI was the minimum about one hour after the meal. Then the AI gradually increased until the measurement was finished three hours after the meal.

The electronic device 100 can estimate the change in blood fluidity based on the change in the calculated AIs. For example, when red blood cells, white blood cells and platelets in the blood all bunched together like a ball or the adhesive force thereof increases, the blood fluidity decreases. For example, when the water content of plasma in the blood decreases, the blood fluidity decreases. These changes in the blood fluidity depend on, for example, the subject's health conditions such as glycolipid condition, heat disorder, dehydration or hypothemia. The subject can learn the change in his or her own blood fluidity with the electronic device 100 according to one embodiment before his or her health condition becomes severe. The change in AIs before and after the meal illustrated in FIG. 11 allows the subject to estimate the decrease in blood fluidity after the meal, the decrease in the blood fluidity to the minimum about an hour after the meal and a subsequent gradual increase in the blood fluidity. The electronic device 100 may notify the subject of a low blood fluidity condition as "thick" and a high blood fluidity condition as "thin." For example, the electronic device 100 may determine whether "thick" or "thin" based on the AI average value of the subject's actual age. The electronic device 100 may determines the blood as "thin" when the calculated AI is greater than the average value and as "thick" when it is smaller than the average value. For example, the electronic device 100 may determine whether "thick" or "thin" based on the AI before the meal. The electronic device 100 may estimate the degree of "thick" blood based on a comparison between the AI before the meal and that after the meal. For example, the electronic device 100 may use the vascular age (vessel hardness) of the subject as AI before the meal, that is, AI at fasting. For example, the electronic device 100 can decrease estimation errors by the vascular age (vessel hardness) of the subject by calculating the change in the calculated AIs based on the AI of the subject before the meal, that is, the AI at fasting. Thus the electronic device 100 can estimate the change in blood fluidity with a higher accuracy.

Figure 12:
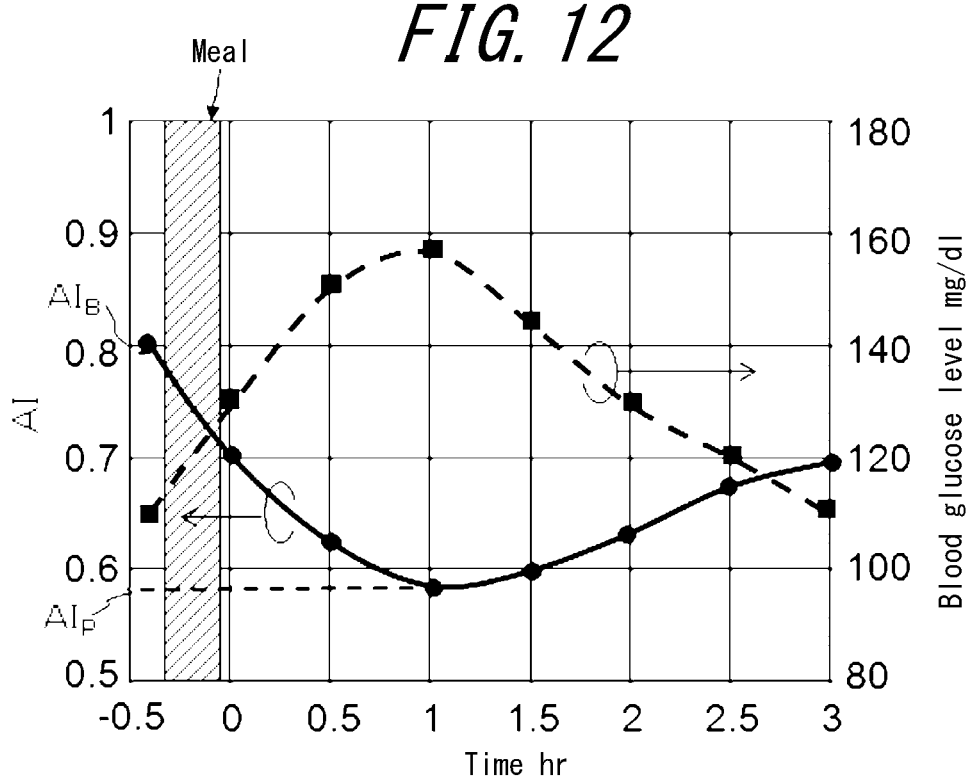
FIG. 12 is a diagram illustrating the calculated AIs and measurement results of blood glucose level.

FIG. 12 is a diagram illustrating the calculated AIs and the measurement results of blood glucose level. The method of acquiring pulse wave and of calculating AI are the same as those according to the embodiment illustrated in FIG. 11. In FIG. 12, the vertical axis on the right represents the blood glucose level and the vertical axis on the left represents the calculated AIs. In FIG. 12, the solid line represents the AI calculated based on the acquired pulse wave and the dotted line represents the measured blood glucose level. The blood glucose level is measured immediately after acquiring the pulse wave. The blood glucose level was measured with a "Medisafe Fit," which is a blood glucose meter by Terumo Co. Compared with the blood glucose level before the meal, the blood glucose level after the meal is increased by about 20 mg/dl. The blood glucose level reached the maximum about one hour after the meal. After that, the blood glucose level gradually decreased until the measurement was finished, and restored to the same blood glucose level as that before the meal about three hours after the meal.

As illustrated in FIG. 12, the blood glucose levels before and after the meal are negatively correlated with the AI calculated from pulse wave. When the blood glucose level increases, the glucose in the blood causes red blood cells and platelets to be agglomerated or to be more sticky, which may cause a decrease in the blood fluidity. A decrease in the blood fluidity may cause a decrease in the pulse wave propagation velocity PWV. A decrease in the pulse wave propagation velocity PWV may cause an increase in the time difference Δt between the forward wave and the reflected wave. An increase in the time difference Δt between the forward wave and the reflected wave may cause a decrease in the height of reflected wave $P_R$ relative to that of forward wave $P_F$. A decrease in the height of reflected wave $P_R$ relative to that of forward wave $P_F$ may cause a decrease in AI. The AI in a few hours after the meal (three hours in one embodiment) correlates with the blood glucose level, and thus a change in the subject's blood glucose level can be estimated. When the subject's blood glucose level is measured and its correlation with the AI is acquired in advance, the electronic device 100 can estimate the subject's blood glucose level from the calculated AI.

The electronic device 100 can estimate the carbohydrate metabolism condition of the subject based on the time at which $AI_P$, which is the minimum AI value detected first after the meal, occurs. The electronic device 100 estimates the blood glucose level as the carbohydrate metabolism condition, for example. As an example of estimation of the carbohydrate metabolism condition, the electronic device 100 can estimate that the subject will have a disorder of carbohydrate metabolism (diabetes) when the minimum AI value, $AI_P$, which is detected first after the meal, is detected after a predetermined period of time (e.g. about one and a half hours after the meal).

The electronic device 100 can estimate the carbohydrate metabolism condition of the subject based on the difference $(AI_B-AI_P)$ between $AI_B$, which is AI before the meal, and $AI_P$, which is the minimum AI value detected first after the meal. As an example of estimation of the carbohydrate metabolism condition, the electronic device 100 can estimate that the subject will have a disorder of carbohydrate metabolism (postprandeial hyperglycemia) if the resulting value of $(AI_B-AI_P)$ is greater than or equal to the predetermined value (e.g. 0.5 or more).

Figure 13:
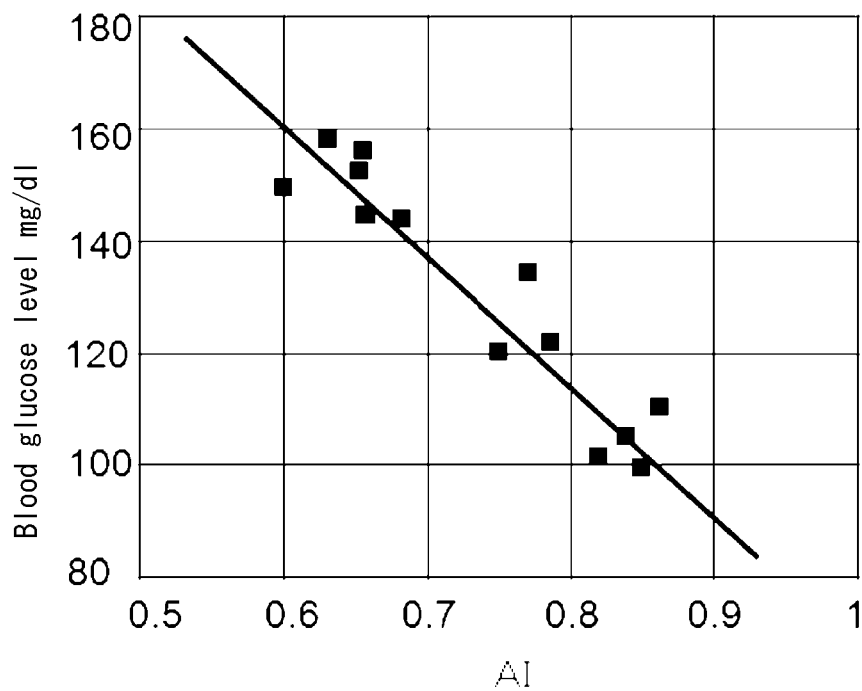
FIG. 13 is a diagram illustrating a relationship between calculated AIs and blood glucose level.

FIG. 13 is a diagram illustrating a relationship between the calculated AI and the blood glucose level. The calculated AI and the blood glucose level are acquired within one hour after the meal, during which the blood glucose level changes a lot. FIG. 13 includes multiple data after the meal acquired from the same subject. As illustrated in FIG. 13, the calculated AI was negatively correlated with the blood glucose level. The coefficient of correlation between the calculated AI and the blood glucose level was 0.9 or more. For example, when the correlation between the calculated AI and the blood glucose level for each subject is acquired in advance as illustrated in FIG. 13, the electronic device 100 can also estimate the subject's blood glucose level from the calculated AI.

Figure 14:
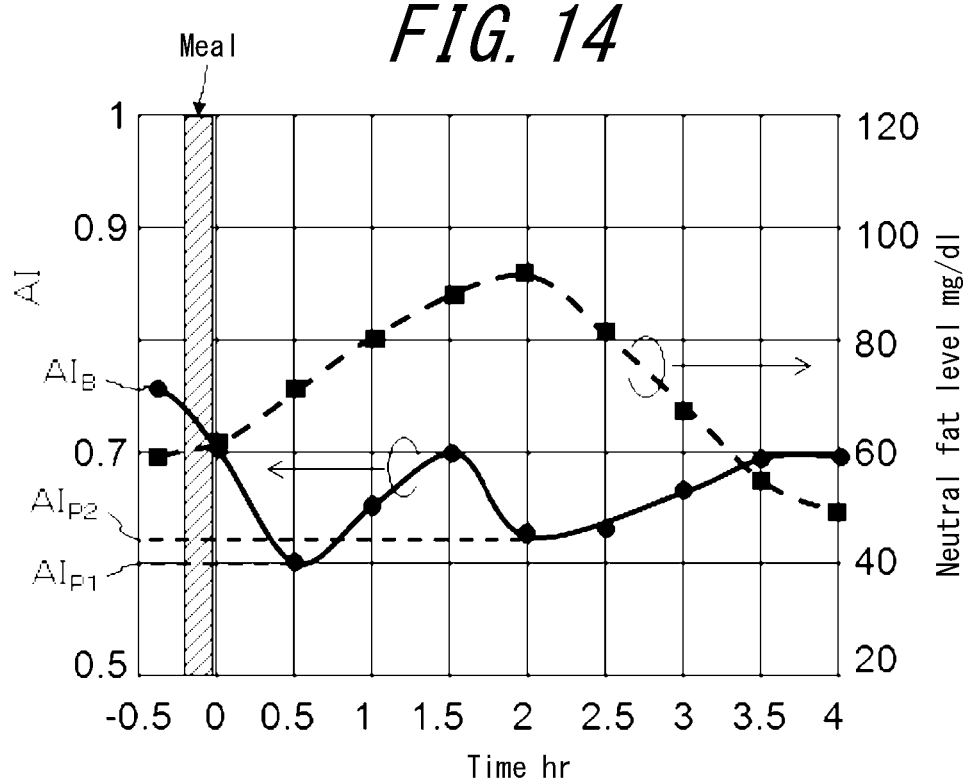
FIG. 14 is a diagram illustrating a relationship between calculated AIs and measurement results of neutral fat level.

FIG. 14 is a diagram illustrating the calculated AI and the neutral fat level. The method of acquiring the pulse wave and the method of calculating AI are the same as those according to the embodiment illustrated in FIG. 11. In FIG. 14, the vertical axis on the right represents the neutral fat level in the blood and the vertical axis on the left represents AI. In FIG. 14, the solid line represents the AI calculated from the acquired pulse wave and the dotted line represents the measured neutral fat level. The neutral fat level is measured immediately after the acquisition of pulse wave. The neutral fat level is measured with a "PocketLipid," which is a lipid analyzer by Techno Medica Co. Compared with the neutral fat level before the meal, the maximum neutral fat level after the meal is increased by about 30 mg/dl. The neutral fat level reached the maximum two hours after the meal. After that, the neutral fat level gradually decreased until the measurement was finished, and restored to the same neutral fat level as that before the meal three and a half hours after the meal.

Whereas, for the calculated minimum AI values, the first minimum value $AI_{P1}$ was detected 30 minutes after the meal and the second minimum value $AI_{P2}$ was detected two hours after the meal. The first minimum value $AI_{P1}$ detected 30 minutes after the meal may have been caused by the effects of the blood glucose level after the meal described above. The second minimum value $AI_{P2}$ detected about two hours after the meal occurred almost at the same time as that at which the maximum value of the neutral fat was detected about two hours after the meal. Thus, the second minimum value $AI_{P2}$ detected later than a predetermined time after the meal can be estimated to have been caused by the effects of the neutral fat. As in the case with the blood glucose level, we found that the neutral fat level before and after the meal is negatively correlated with the AI calculated from the pulse wave. In particular, the minimum AI value, $AI_{P2}$, detected later than the predetermined hours (in one embodiment, about one and a half hours) after the meal is correlated with the neutral fat level, and thus a change in the subject's neutral fat level can be estimated based on a change in AI. When the subject's neutral fat level is measured and its correlation with the AI is acquired in advance, the electronic device 100 can estimate the subject's neutral fat level from the calculated AI.

The electronic device 100 can estimate the subject's lipid metabolism condition based on the time at which $AI_{P2}$, which is the second minimum value detected later than a predetermined time after the meal, occurs. The electronic device 100 estimates, for example, the lipid level as the lipid metabolism condition. As an example of estimation of the lipid metabolism condition, the electronic device 100 can estimate that the subject will have a disorder of lipid metabolism (hyperlipidemia) when the second minimum value $AI_{P2}$ is detected later than a predetermined period of time (e.g. about four hours or more) after the meal.

The electronic device 100 can estimate the subject's lipid metabolism condition based on the difference between $AI_B$, which is AI before the meal, and $AI_{P2}$, which is the second minimum value detected later than a predetermined time after the meal $(AI_B-AI_{P2})$. As an example of estimation of the abnormal lipid metabolism condition, the electronic device 100 can estimate that the subject will have a disorder of lipid metabolism (postprandial hyperlipidemia) if the resulting value of $(AI_B-AI_{P2})$ is 0.5 or more.

Based on the measurement results illustrated from FIGS. 12 to 14, the electronic device 100 according to one embodiment can estimate the subject's carbohydrate metabolism condition based on the first minimum value $AI_{P1}$ to be detected earliest after the meal and the time at which it occurs. The electronic device 100 according to one embodiment can also estimate the subject's lipid metabolism condition based on the second minimum value $AI_{P2}$ detected later than a predetermined time after the first minimum value $AI_{P1}$ and the time at which it occurs.

According to one embodiment, although an example of neutral fat has been explained as an example of estimating the lipid metabolism, estimation of the lipid metabolism is not limited to the neutral fat. The lipid level to be estimated by the electronic device 100 includes, for example, a total cholesterol, a high density lipoprotein (HDL) cholesterol and a low density lipoprotein (LDL) cholesterol. These lipid levels exhibit the same tendency as that of the neutral fat.

Figure 15:
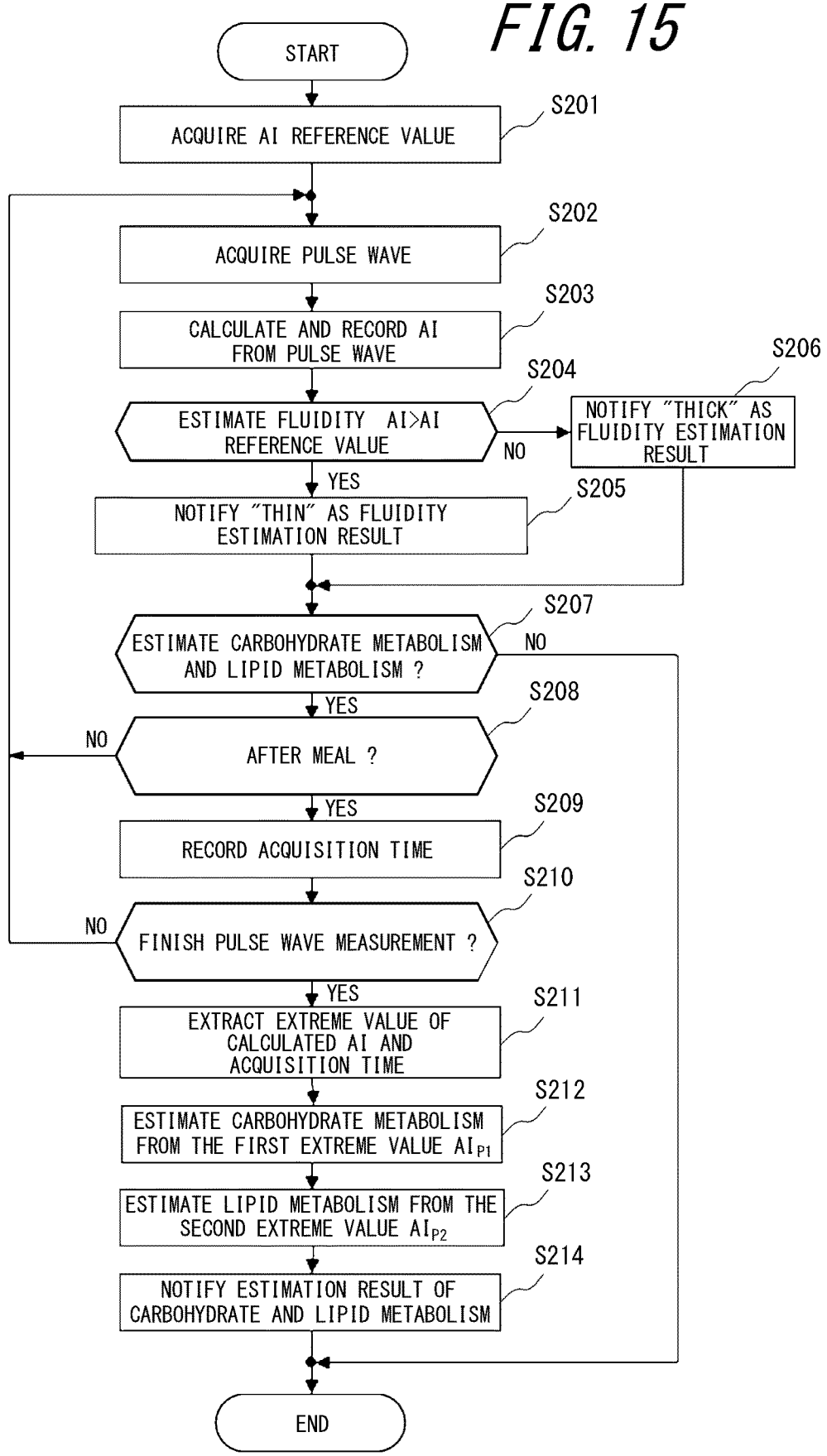
FIG. 15 is a flow chart illustrating a procedure for estimating blood fluidity and conditions of carbohydrate metabolism and lipid metabolism.

FIG. 15 is a flowchart illustrating a procedure of estimating the blood fluidity and the conditions of the carbohydrate metabolism and the lipid metabolism based on AI. A flow for estimating the blood fluidity and the conditions of the carbohydrate metabolism and the lipid metabolism with the electronic device 100 according to one embodiment will be described with reference to FIG. 15.

As illustrated in FIG. 15, the electronic device 100 acquires the AI reference value of the subject as a default (step S201). As the AI reference value, an average AI estimated from the age of the subject or the AI of the subject at fasting acquired in advance may be used. The electronic device 100 may use the AI determined as that before the meal from steps S202 to S208 as the AI reference value, or the AI calculated immediately before the measurement of pulse wave as the AI reference value. In this case, the electronic device 100 executes step S201 after steps from S202 to S208.

Subsequently, the electronic device 100 acquires the pulse wave (step S202). For example, the electronic device 100 determines whether the pulse wave acquired in a predetermined measurement period of time (e.g. 5 seconds) has an amplitude greater or equal to a predetermined amplitude. When the acquired amplitude is greater or equal to the predetermined amplitude, the process proceeds to step S203. If the predetermined amplitude is not acquired, the process repeats step S202 (these steps not illustrated). In step S202, when the electronic device 100 detects a pulse wave greater than or equal to the predetermined amplitude, for example, it automatically acquires the pulse wave.

The electronic device 100 calculates the AI as an index based on pulse wave from the pulse wave acquired in step S202 and stores the AI in the memory 145 (step S203). The electronic device 100 may calculate the average $AI_{ave}$ from the $AI_n$ (n is an integer from 1 to n) for each predetermined number of pulses (e.g. three pulses) and determine it as AI. Alternatively, the electronic device 100 may calculate the AI at a specific pulse.

AI may be corrected by the number of pulses PR, pressure pulse ($P_F$–$P_S$), body temperature, temperature of the region to be detected or the like. Both the pulse and the AI and the pulse pressure and the AI have been known to have a negative correlation and the temperature and the AI have been known to have a positive correlation. When the AI is corrected, the electronic device 100 calculates the pulse and the pulse pressure in addition to the AI in step S203, for example. In the electronic device 100, a temperature sensor may be mounted on the sensor unit 130 to acquire the temperature of the portion to be detected when a pulse wave is acquired in step S202. The acquired pulse, pulse pressure, temperature, or the like, may be assigned to the formula for correction prepared in advance to allow the electronic device 100 to correct AI.

Subsequently, the electronic device 100 compares the AI reference value acquired in step S201 and the AI calculated in step S203 to estimate the blood fluidity of the subject (step S204). When the calculated AI is greater than the AI reference value (if YES), the blood fluidity is estimated to be high. In this case, the electronic device 100 may notify that "the blood is thin," for example (step S205). When the calculated AI is not greater than the AI reference value (if NO), the blood fluidity is estimated to be low. In this case, the electronic device 100 may notify that "the blood is thick," for example (step S206).

Subsequently, the electronic device 100 confirms with the subject about whether to estimate the carbohydrate metabolism and lipid metabolism conditions (step S207). If the carbohydrate metabolism and the lipid metabolism are not estimated in step S207 (if NO), the process ends. If the carbohydrate metabolism and the lipid metabolism are estimated in step S207 (if YES), the electronic device 100 confirms whether the calculated AI is acquired before or after the meal (step S208). If not after the meal (before the meal) (if NO), the process returns to step S202 to acquire the next pulse wave. If after the meal (if YES), the electronic device 100 stores the time at which the pulse wave corresponding to the calculated AI is acquired (step S209). When a pulse wave is subsequently acquired (No in step S210), the process returns to step S202 and the electronic device 100 acquires the next pulse wave. When the measurement of pulse wave is finished (YES in step S210), the process proceeds to step S211 or after the step, and the electronic device 100 estimates the conditions of the subject's carbohydrate metabolism and lipid metabolism.

Subsequently, the electronic device 100 extracts the minimum value and its time from the multiple AIs calculated in step S204 (step S211). For example, when the AIs as indicated by the solid line in FIG. 14 are calculated, the electronic device 100 extracts the first minimum value $AI_{P1}$ detected 30 minutes after the meal and the second minimum value $AI_{P2}$ detected about two hours after the meal.

Subsequently, the electronic device 100 estimates the subject's carbohydrate metabolism condition based on the first minimum value $AI_{P1}$ and its time (step S212). Further, the electronic device 100 estimates the subject's lipid metabolism condition based on the second minimum value $AI_{P2}$ and its time (step S213). An example of estimation of the subject's carbohydrate metabolism and lipid metabolism conditions are the same as that of FIG. 14, and thus is omitted.

Subsequently, the electronic device 100 notifies the estimation results acquired in steps S212 and S213 (step S214) and the process ends the flow illustrated in FIG. 15. The notification interface 147 may notify some pieces of information including "the carbohydrate metabolism is normal," "the carbohydrate metabolism may be abnormal," "the lipid metabolism is normal" and "the lipid metabolism may be abnormal." The notification interface 147 may also notify some pieces of advice including "go to see a doctor," "review your eating habits." Then the electronic device 100 causes the process illustrated in FIG. 15 to end.

Thus, according to the electronic device 100 of the present embodiment, estimation of the carotid artery condition, the blood fluidity, and the carbohydrate metabolism or lipid metabolism condition can be executed by a single device. In particular, the electronic device 100 can estimate the blood fluidity and the conditions of the carbohydrate metabolism and the lipid metabolism of the subject in a quick and non-invasive manner.

The electronic device 100 can estimate the carbohydrate metabolism and the lipid metabolism conditions from the extreme values of the index based on the pulse wave and its time. Thus the electronic device 100 can estimate the subject's carbohydrate metabolism and lipid metabolism conditions in a quick and non-invasive manner.

The electronic device 100 can estimate the subject's carbohydrate metabolism and lipid metabolism conditions from the index based on pulse wave before the meal (at fasting), for example. Thus the electronic device 100 can correctly estimate the blood fluidity and the conditions of the carbohydrate metabolism and the lipid metabolism of the subject without considering the diameter or the hardness of the blood vessel that will not change in a short period of time.

When calibrations of the index based on pulse wave and the blood glucose level and the lipid level are performed in advance, the electronic device 100 can estimate the subject's blood glucose level and lipid level in a quick and non-invasive manner.

Figure 16:
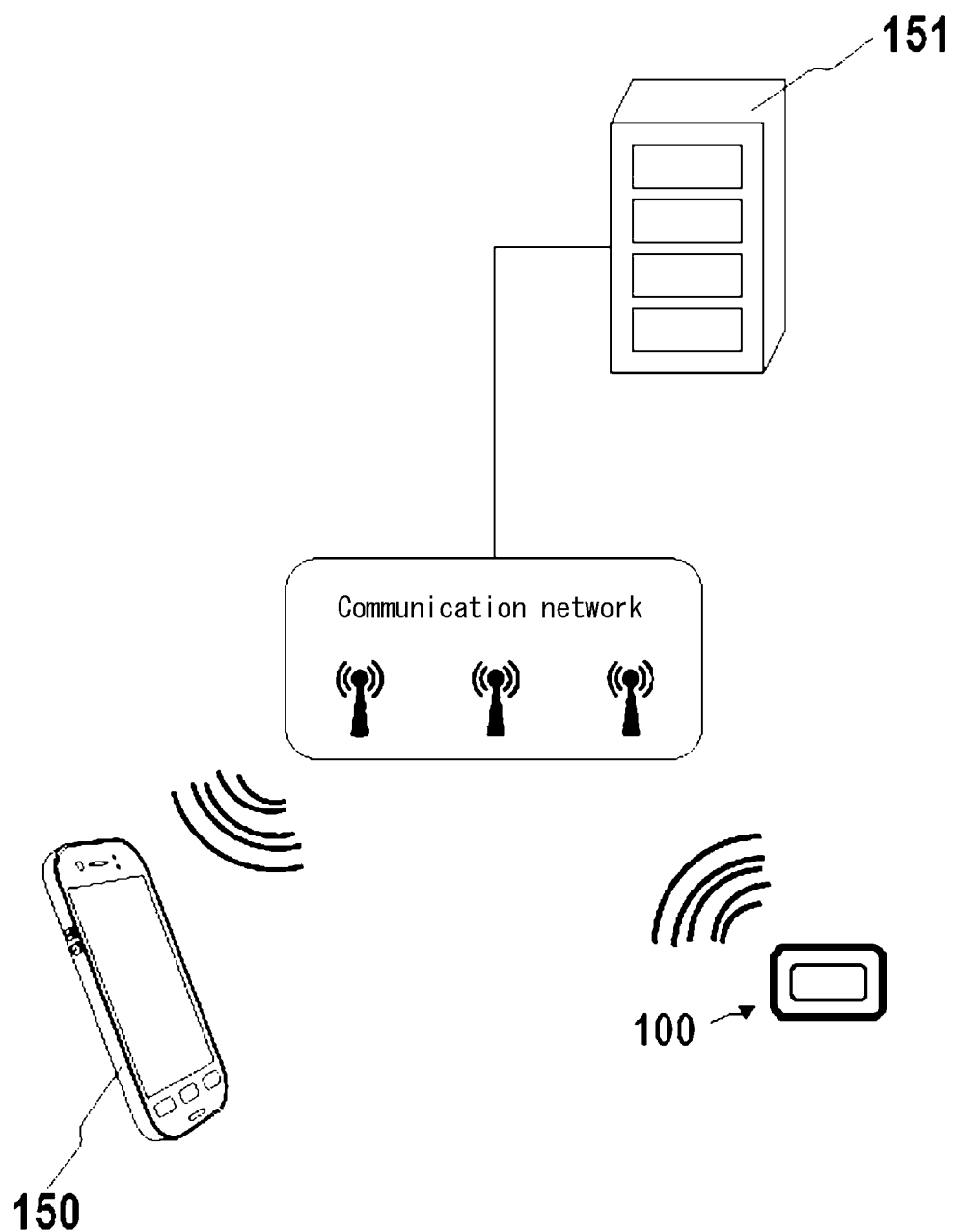
FIG. 16 is a schematic diagram illustrating a schematic configuration of an estimation system according to one embodiment.

FIG. 16 is a schematic diagram illustrating a schematic configuration of an estimation system according to one embodiment. The estimation system according to one embodiment illustrated in FIG. 16 includes the electronic device 100, a server 151, which is an estimation device, a mobile terminal 150 and a communication network. As illustrated in FIG. 16, the pulse wave acquired by the electronic device 100 is transmitted to the server 151 over the communication network and is stored in the server 151 as the subject's personal information. In the server 151, the subject's carotid artery condition is estimated based on the comparison with the subject's information acquired in the past or various databases. Further, the server 151 produces the most suitable advice for the subject. The server 151 replies the estimation results and advice to the subject's mobile terminal 150. The mobile terminal 150 displays the received estimation results and advice on the display of the mobile terminal 150. Information from users can be collected in the server 151 by using the communication function of the electronic device 100, and thus the estimation system can further improve the estimation accuracy. Since the mobile terminal 150 is used as a notification means, the electronic device 100 does not need the notification interface 147 any more, and thus can be downsized furthermore. Since estimation of the carotid artery condition is performed by the server 151, calculation burden on the controller 143 of the electronic device 100 is reduced. Since the information of the subject acquired in the past can be stored in the server 151, burden on the memory 145 of the electronic device 100 is reduced. These allow for further downsizing and simplification of the electronic device 100 and improvement in the arithmetic processing speed. The estimation system can also estimate the subject's blood fluidity, carbohydrate metabolism and lipid metabolism in the same manner as described above.

The estimation system according to one embodiment is configured by connecting the electronic device 100 and the mobile terminal 150 over the communication network via the server 151. However, the estimation system is not limited thereto. In the estimation system according to one embodiment, the electronic device 100 and the mobile terminal 150 may be connected directly over the communication network without using the server 151.

Some embodiments have been described so that the present disclosure will be disclosed completely and clearly. However, the accompanying claims should not be limited to the above described embodiments, and should be configured to embody all changes and alternative configurations conceivable by those skilled in the art in the scope of the basis disclosed in this specification. Each requirement disclosed in some embodiments may be combined in any manner.

For example, in the above described one embodiment, the sensor unit 130 includes the angular velocity sensor 131. However, the electronic device 100 is not limited thereto. The sensor unit 130 may include an optical pulse wave sensor comprising a light emitting unit and a light receiving unit, or include a pressure sensor. The position (measured part) from which a pulse wave is acquired with the electronic device 100 for estimating the blood fluidity, carbohydrate metabolism or lipid metabolism conditions is not limited to the neck. The sensor unit 130 may be put to the artery of wrist, ankle, thigh, ear, or the like, to acquire a pulse wave for estimating the blood fluidity, carbohydrate metabolism or lipid metabolism conditions.

In the above described one embodiment, the natural frequency of the sensor unit 130 may be configured so that it will be close to the frequency of the pulse wave to be acquired. For example, when the frequency of the pulse wave to be acquired is from 0.5 to 2 Hz (pulse from 30 to 120), the sensor unit 130 may have any natural frequency in the range from 0.5 to 2 Hz. The natural frequency of the sensor unit 130 can be optimized by changing the length and the weight of the sensor unit 130 and the elastic modulus or the spring constant of the elastic member 140. Optimization of the natural frequency of the sensor unit 130 allows the electronic device 100 to measure with a higher accuracy.

The invention claimed is:

1. An electronic device, comprising:
    a sensing plate including at least one sensor configured to acquire a pulse wave of a subject's carotid artery;
    a spring configured to be disposed substantially perpendicular to the subject's carotid artery to press the sensing plate such that the sensing plate presses skin over the subject's carotid artery, and that the sensing plate is displaced in response to a movement of the subject's carotid artery;
    a housing;
    a shaft that fastens a first end of the sensing plate to the housing of the electronic device such that the sensing plate is configured to be rotated with respect to the shaft, and that a second end of the sensing plate is displaceable in the direction substantially vertical to a plane of a back side of the electronic device; and
    a processor configured to estimate a condition of the subject's carotid artery based on the pulse wave acquired by the at least one sensor, wherein the at least one sensor comprises an angular velocity sensor positioned closer to the first end of the sensing plate than the second end of the sensing plate.

2. The electronic device according to claim 1, wherein the condition of the carotid artery is a degree of arteriosclerosis of the carotid artery.

3. The electronic device according to claim 1, wherein the processor calculates a dicrotic notch of the pulse wave acquired by the at least one sensor and estimates the condition of the carotid artery based on the calculated dicrotic notch.

4. An estimation system, comprising:
    an electronic device that includes: a sensing plate including at least one sensor configured to acquire a pulse wave of a subject's carotid artery; a spring configured to be disposed substantially perpendicular to the subject's carotid artery to press the sensing plate such that the sensing plate presses skin over the subject's carotid artery, and that the sensing plate is displaced in response to a movement of the subject's carotid artery; a housing; and a shaft that fastens a first end of the sensing plate to the housing of the electronic device such that the sensing plate is configured to be rotated with respect to the shaft, and that a second end of the sensing plate is displaceable in the direction substantially vertical to a plane of a back side of the electronic device; and an estimation device that includes a processor configured to estimate a condition of the subject's carotid artery based on the pulse wave acquired by the at least one sensor, wherein the at least one sensor comprises an angular velocity sensor positioned closer to the first end of the sensing plate than the second end of the sensing plate.

5. The electronic device according to claim 1, wherein the processor is further configured to:

determine whether stable pulse waves have been detected for a predetermined number of times in succession after a start of a pulse wave measurement processing; and when the processor determines that the stable pulse waves have been consecutively detected for the predetermined number of times after the start of the pulse wave measurement processing, acquire the pulse wave via the at least one sensor and estimate the condition of the subject's carotid artery based on the pulse wave acquired by the at least one sensor.

* * * * *